United States Patent [19]

Arrance, Sr.

[11] 4,282,081
[45] Aug. 4, 1981

[54] DOUBLE JUNCTION REFERENCE ELECTRODE

[75] Inventor: Frank C. Arrance, Sr., Costa Mesa, Calif.

[73] Assignee: Graphic Controls Corp., Buffalo, N.Y.

[21] Appl. No.: 167,768

[22] Filed: Jul. 10, 1980

[51] Int. Cl.³ ............................................. G01N 27/30
[52] U.S. Cl. ................................................. 204/195 F
[58] Field of Search .................... 204/195 F; 324/438; 128/635

[56] References Cited

U.S. PATENT DOCUMENTS 3,103,480   9/1963   Watanabe et al. ............... 204/195 F
3,455,793   7/1969   Watanabe et al. ............ 204/195 F X Primary Examiner—G. L. Kaplan
Attorney, Agent, or Firm—Kegan, Kegan & Berkman

[57] ABSTRACT

A highly stable, double-junction, modular reference electrode for assay of low-level halide concentrations, sulfides, perchlorates, silver, mercury, and other heavy metals, and including upper and lower axially in-line, readily accessible and conveniently fillable compartments for retaining electrically conductive compositions, an intercoupling removable plug constituting fluid-tight means bridging axially between the compartments and carrying a conduit providing a fluid permeable electrically and ionically conductive path between the compartments, an external cable lead projecting through a sealing cap closing the upper compartment for establishing electrical contact with a conductive medium contained in the upper compartment, a removable sealing plug at a lower open end of the lower compartment, and a conduit extending axially through said plug and providing a flow-restrictive fluid permeable path between the lower compartment and a test system external of the electrode.

10 Claims, 5 Drawing Figures

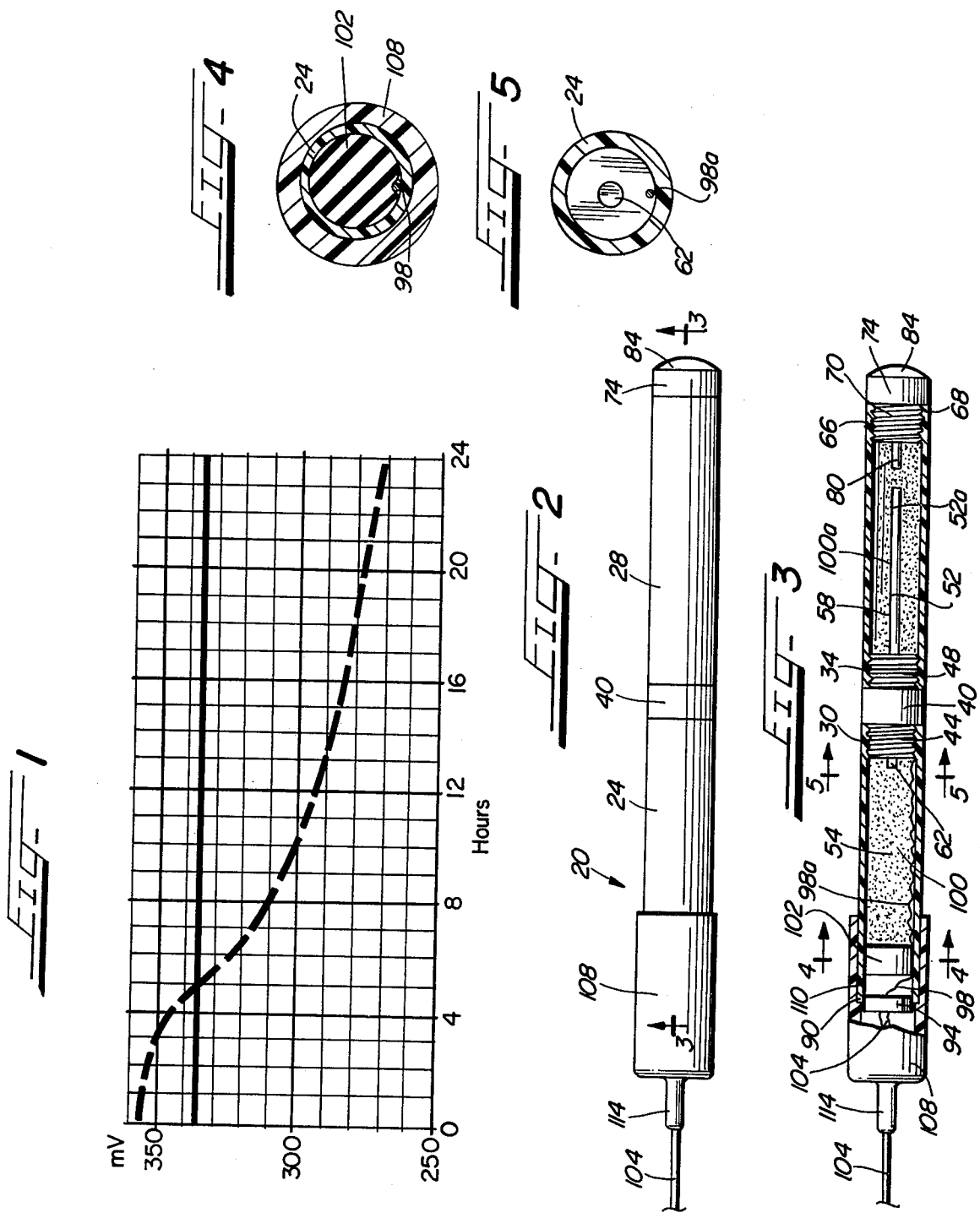

DOUBLE JUNCTION REFERENCE ELECTRODE

BACKGROUND OF THE INVENTION

This invention relates to improvements in electrodes of the type used for electrochemical detection and measurement of the concentration of ions in solution. More particularly, the invention is directed to an ultrastable, double junction modular reference electrode finding utility in the assay of low level halide concentrations, sulphides, perchlorates, silver, mercury and other heavy metals. Electrodes finding general utility in those areas in which the instant electrodes are useful are known in the prior art. Such electrodes have taken various physical constructions, and for many specific arrangements certain advantages have been claimed. However, each prior art structure has one or more disadvantages or inadequacies, and none has proven completely suitable for its intended use. For example, may of the electrodes utilize internal solutions or compositions which serve as electrically conductive media. The introduction of such solutions has posed procedural and assembly problems. Additionally, the need periodically to replenish or replace the liquid-like or fluid filler composition dictates the provision of practical access means or sealable ports. A related desirable capability is the ease of disassembly and reassembly of the entire structure for cleaning and for such part replacement as may be desirable or necessary.

Still another important goal of electrodes of the type to which the instant invention is directed is to achieve a minimum of diffusion or escape of the fluid contents from the interior of the electrode proper, thereby to insure reproducibility of results and electrode stability. The extensive investigative and research work carried out in this field, notwithstanding, no electrode developed has been found to be completely satisfactory in all respects. It is, therefore, the aim of the present invention to provide an improved double junction reference electrode which constitutes a structural combination obviating many of the shortcomings of the prior art devices and enabling the realization of advantages and reproduceability in use not heretofore achievable.

SUMMARY OF THE INVENTION

In accordance with the practice of the instant invention there is provided a highly stable, double-junction modular reference electrode having a broad area of utility and useful in the potentiometric assay in solutions comprized of low level halide concentrations, sulphides, perchlorates, silver, mercury, and other heavy metals. It is useful for measuring there but also for measuring other species in the presence of these, for example—measuring hydrogen ions in the presence of sulfide ions.

It is an important feature of the electrode of the invention that it provides a reproducible and stable potential when used in combination with other electrodes or equivalent structures.

It is a related feature of the invention that the electrode exhibits such desirable properties as reversibility, reproducibility, and stability. The electrode is characterized as a suitable conductor for the high ($\geqq 10^6\Omega$) impedance electrical signal generated at the solution boundary with a cooperating, measuring electrode.

It is an important structural feature of the electrode of the invention that it may be readily disassembled, cleaned, refilled, and reassembled without the use of special tools, and without any need for special technical training.

A significant technical advantage of the electrode of the invention is that it provides a precise and reproducible reference potential over a long time period. Diffusion of silver and chloride ions from the upper compartment through the lower compartment to the external solution from the electrode is essentially non-measurable for over 240 hours when the measuring system consists of a $Hg_2Cl_2$-$HgS$ "solid state" chloride electrode and this reference electrode, when the external solution is 100 ml of $18 \times 10^6 \Omega$ water.

Novel structural features of the electrode which contribute to its versatility, stability, ease of assembly, and ease of replacement of parts, simplified filling and refilling of the various chambers with conductive compositions, absence of leakage and avoidance of test solution contamination, avoidance of "plugging" problems, physical strength and reliability in use, derive from structural features and arrangements including the following:

(a) separate upper and lower compartments for electrolyte compositions.

(b) threaded intercoupling plug for interconnecting the upper and the lower compartments in coaxial serial relationship.

(c) a threaded plug as a mechanical seal for the base of the lower compartment.

(d) the use of liquid flow restricting conduits carried by the intercoupling plug joining the upper and lower compartments and providing an electrically conductive path between the compartments.

(e) the use of liquid flow restricting conduits, carried by the base plug of the electrode and establishing electrical communication between the interior of the lower compartment and the exterior, test solution.

(f) a protective cap sealed to and surmounting the upper extremity of the upper compartment and carrying a wire communicating between the upper compartment and the exterior of the electrode.

The overall combination which constitutes the improved electrode of the invention is characterized by proved stability, reliability, useful life, and simplicity of operation and maintenance.

Other and further objects, features and advantages of the invention will be evident from the following description considered in conjunction with the drawing.

BRIEF DESCRIPTION OF THE DRAWING

FIG. 1 is a graphic representation comparing the stability of the double junction reference of the invention with that of a standard corresponding type of electrode of the prior art, the former being shown in solid line and the latter in broken line;

FIG. 2 is a side elevational view of a double junction reference electrode in accordance with the invention;

FIG. 3 is a cross-sectional view taken substantially on the lines 3—3 of FIG. 2 and showing the internal structure of the electrode assembly of the invention;

FIG. 4 is a cross-sectional view taken substantially on the lines 4—4 of FIG. 3; and FIG. 5 is a cross-sectional view taken substantially on the lines 5—5 of FIG. 3.

DESCRIPTION OF THE PREFERRED EMBODIMENT

In accordance with the invention, the aims and objects are achieved by providing a reference electrode which includes an in-line series of two compartments joined mechanically and electrically through a double-ended threaded coupling. Communication between the two distinct compartments is insured, electrically, by means of a fluid flow limiting electrically conducting conduit projecting at its opposite ends into the two separate and distinct chambers or compartments of the electrode. The lower compartment is provided with a sealing plug which includes an electrically conductive conduit or core communicating between the lower compartment and the exterior or the ambient system. At its upper end, a lead line is connected to the upper extremity of the upper compartment, the line establishing electrical communication between the interior of the upper compartment and an external test apparatus.

The double junction electrode described provides a percise and reproducible reference potential for a long period of time. In testing over a 240 hour period, and starting with a $10^{-7}$ Molar (3.5 ppb) chloride solution, no detectable transfer of chloride occurred between the electrode and the test system. The electrode fulfills a long-felt need, especially when measuring a low chloride concentrations, since the described structure effectively prevents both silver and chloride contamination of the solution being analyzed.

Being of rugged, all-plastic polymer, modular construction, the electrode components are separable at threaded junctions, allowing easy access to both the upper and lower chambers for thorough cleaning and convenient refilling. Developed originally for use with ion selective electrodes, the double junction reference electrode of the present invention may be effectively used for electrochemical measurements where silver, mercury, lead or sulphide ion contamination would ordinarily present a junction plugging problem.

In a typical functional embodiment of the electrode of the invention, the upper compartment is filled with a gelled saturated solution of potassium chloride saturated with silver chloride and the lower compartment is filled with a gelled saturated solution of potassium nitrate. Other suitable conducting fluids or gels, both aqueous and non-aqueous, may be used. A typical gelling agent may be hydroxyethylcellulose.

A principal and important feature of the electrode of the invention is an exceedingly minute chloride leakage rate from the upper compartment to the lower compartment and from the lower compartment to the external, test solution. This minimal leakage rate is indicated graphically in FIG. 1, which shows no significant leakage over a 24-hour period. Actually, there is no significant leakage over a 240-hour period. In the same figure, the instability of prior art electrodes is shown as a drop in the voltage charge over the 24-hour test period. This decrease in charge is correlated with the leaking of chloride ions.

Referring now to the drawings, and particularly to FIGS. 2 and 3, for purposes of disclosure, the subject invention is shown embodied as an electrode assembly 20 including a pair of in-line, coaxial, vertically-oriented sealable tubular fluid retaining compartments depicted as an upper compartment 24 and a lower compartment 28, each of a generally cylindrical, tubular configuration. The two cylindrical compartments 24 and 28 are joined to one another at an internally threaded lower end 30 of the upper compartment and at an internally threaded upper end 34 of the lower compartment by means of a coupler or plug 40 formed at its opposed ends with exterior threads 44 and 48 for mating interengagement in fluid-tight sealing relationship with the coresponding threads 30 and 34 of the upper and the lower compartments.

Sealingly secured coaxially within the coupling plug 40 is a conduit 52 for establishing electrical continuity between the interior 54 of the upper compartment and the interior 58 of the lower compartment. In the particular form of the electrode illustrated, the conduit 52 is fabricated of a porous ceramic rod material which, while preventing the unrestricted fluid flow therethrough, serves as a liquid-retentive composition functioning as a bridging element between the upper and the lower compartments 54 and 58. As shown, a stub portion 62 of the conduit 52 extends slightly into the upper cavity 54, and a longer portion 52a projects well into the lower compartment 58.

The lower compartment 28 is threaded internally 66 at its lower end 68 and a cooperatively-threaded 70 plug is sealingly secured through the mating threads 66 and 70 in the lower end portion 68 of the lower compartment 28, as shown in FIG. 3. Sealed into to extend through the plug 74 coaxially therewith is a second conduit 80 which projects at its upper end into the lower cavity 58. The conduit 80 terminates at its opposite end so as to be substantially flush with the rounded end portion 84 of the plug 74. Thus, the conduit 80, which is preferably made of porous ceramic, but which may conveniently constitute a capillary tube or the like (as in the case of conduit 52, as well), establishes electrical continuity between the interior of the lower compartment 58 and the ambient system or with a test system exterior of the electrode proper. The conduit means may be made from a material such as ceramics, wood, hydrocarbons, polymers, polyisocyanates, polyurethanes, polyamides, polyesters, polytetrafluoroethylene, polytrifluoro chloroethylene, natural fibers, synthetic fibers and porous glass structures including sintered glass.

The upper, open end 90 of the upper compartment 24 is sealed by means of a resinous, disc-like plug 94 of an epoxy or similar material. Sealed into to extend through the seal 94 is an electrically conductive silver wire 98 coated with silver chloride, or a Ag/AgCl half cell. The wire has a principal bared portion 98a extending well into the upper compartment 54. A disc-like plug 102 of an elastomeric material or of plastic stressingly bears against and seals internally within the upper compartment 20 to retain the conductive fluid or gel 100 within the cavity 54. In the particular embodiment shown, the wire 98 is effectively sealed and secured between the plug 102 and the interior wall surface of the cylindrical tube 24 defining the upper compartment.

At its end projecting outwardly from the electrode assembly, the wire 98 is insulated 104, and a sealing cap 108 frictionally secured to the upper end portion 110 of the upper compartment 24 is provided with an integrally formed stub section 114 provided with an axial through opening through which the insulated wire 104 extends for attachment to external instrumentation, not shown.

What is claimed is:

1. A double junction reference electrode providing a precise and reproducible reference potential stable over at least a 24-hour time period, said electrode comprising a pair of in-line coaxial, vertically-oriented sealable, tubular fluid compartments including an upper compartment and a lower compartment each adapted to retain an electrically conductive chemical composition therein, joinder means coaxial with said upper compartment and with said lower compartment and interposed therebetween for mechanically and dissociably intercoupling said compartments in fluid-tight interengagement with one another, fluid-retentive, fluid-flow-restricting first conduit means supported by and extending axially through said joinder means for providing an ion-permeable electrically conductive fluid path between said upper compartment and said lower compartment, cap means surmounting said upper compartment for sealing an upper open end thereof, to provide a fluid-tight closure therefor, electrically conductive external cable means sealed into to extend through said cap means in electrically conductive communication with said upper compartment interiorly thereof, plug means sealing a lower open end of said lower compartment as a fluid tight closure therefor, fluid permeable second conduit means extending axially through said plug means for providing an electrically conductive fluid-permeable junction between said lower compartment and a test system exterior of said electrode.

2. The structure as set forth in claim 1 wherein said first conduit means extending through said joinder means and said second conduit means extending through said plug means comprises a porous ceramic rod for providing electrical junctions at said upper and said lower compartments.

3. The structure as set forth in claim 1 and further comprising an electrically conductive composition in said upper compartment, and an electrically conductive metallic wire connected to and extending from said cable into said upper compartment for engaging said electrically conductive composition contained therein.

4. The structure as set forth in claim 3 wherein said wire is a silver wire, and further comprising a deposit of silver chloride on a free end of said wire for making electrical contact with said electrically conductive composition contained in said upper compartment.

5. The structure as set forth in claim 1 and further comprising electrically conductive gel means confined as a filling medium in each of said upper compartment and said lower compartment for establishing electrically conductive paths therethrough.

6. The structure as set forth in claim 5 wherein said gel means comprises compositions containing potassium nitrate in the lower compartment and compositions containing potassium chloride, and a gelling agent in the upper compartment.

7. The structure as set forth in claim 6 wherein said gelling agent is hydroxyethylcellulose.

8. The structure as set forth in claim 1 wherein said first and said second conduit means each comprises porous material selected from the group consisting of ceramics, wood, hydrocarbons, polyisocyanates, polyurethanes, polyamides, polyesters, polytetrafluoroethylene, polytrifluoro chloroethylene, natural fibers, synthetic fibers, and porous glass structures including sintered glass.

9. The structure as set forth in claim 1 wherein said second conduit means includes an orifice of capillary dimensions at a base of said lower compartment.

10. The structure as set forth in claim 1 and further comprising an electrically conductive saturated salt solution, in gel form, in each of said upper compartment and said lower compartment.

* * * * *